United States Patent
Weber et al.

(10) Patent No.: US 7,914,454 B2
(45) Date of Patent: *Mar. 29, 2011

(54) REAL-TIME 3D ULTRASONIC IMAGING APPARATUS AND METHOD

(75) Inventors: Peter Weber, Dundas (CA); Timothy J Nohara, Fonthill (CA); Al-Nasir Premji, St. Catherines (CA)

(73) Assignee: Wilk Ultrasound of Canada, Inc., Toronto, Ontario (CA)

( * ) Notice: Subject to any disclaimer, the term of this patent is extended or adjusted under 35 U.S.C. 154(b) by 1914 days.

This patent is subject to a terminal disclaimer.

(21) Appl. No.: 10/876,743

(22) Filed: Jun. 25, 2004

(65) Prior Publication Data

US 2005/0288588 A1    Dec. 29, 2005

(51) Int. Cl.
*A61B 6/00* (2006.01)
(52) U.S. Cl. ........ 600/443; 600/447; 600/437; 600/407; 600/454; 600/455
(58) Field of Classification Search .................. 600/443, 600/407, 437
See application file for complete search history.

(56) References Cited

U.S. PATENT DOCUMENTS

| | | |
|---|---|---|
| 3,552,382 A | 1/1971 | Mount |
| 3,805,596 A | 4/1974 | Klahr |
| 3,927,662 A | 12/1975 | Ziedonis |
| 4,048,616 A | 9/1977 | Hart et al. |
| 4,149,420 A | 4/1979 | Hutchison et al. |
| 4,315,514 A | 2/1982 | Drewes et al. |
| 4,446,740 A | 5/1984 | Wilson et al. |
| 4,623,219 A | 11/1986 | Trias |
| 4,646,158 A | 2/1987 | Ohno et al. |
| 4,671,293 A | 6/1987 | Shaulov |
| 4,757,820 A | 7/1988 | Itoh |
| 4,771,786 A | 9/1988 | Iinuma |
| 4,819,649 A | 4/1989 | Rogers et al. |
| 4,991,604 A | 2/1991 | Wurster et al. |
| 5,078,143 A | 1/1992 | Okazaki et al. |
| 5,091,893 A | 2/1992 | Smith et al. |
| 5,099,459 A | 3/1992 | Smith |
| 5,099,848 A | 3/1992 | Parker et al. |

(Continued)

OTHER PUBLICATIONS

Elevation Performance of 1.25D and 1.5D Transducer Arrays; by Douglas G. Wildes, et al.; IEEE Transactions on Ultrasound, Ferroelectronics and Frequency Control, vol. 44. No. 5, Sep. 1997; pp. 1027-1036.

(Continued)

*Primary Examiner* — Brian Casler
*Assistant Examiner* — Joel M Lamprecht
(74) *Attorney, Agent, or Firm* — R. Neil Sudol; Henry D. Coleman; William J. Sapone

(57) ABSTRACT

A method and apparatus for electronic volume data acquisition using ultrasound generates image data in a scanning and imaging process known as coherent aperture combining beamforming (CAC-BF). The CAC-BF technique can be applied in an azimuth dimension and/or an elevation dimension, to form an ultrasound image line, image plane, or image data cube. Several innovations relating to the design and ordering of shots and efficient weighting algorithms that address various performance issues associated with B-mode and other modes such as Doppler, and harmonic imaging are disclosed. The invention has significant advantages over other synthetic aperture imaging techniques and conventional imaging techniques by supporting higher resolution, larger volumes and/or shorter acquisition times than comparative techniques, using similar system hardware complexity.

29 Claims, 5 Drawing Sheets

U.S. PATENT DOCUMENTS

| | | | |
|---|---|---|---|
| 5,135,001 A | 8/1992 | Sinofsky et al. |
| 5,163,436 A | 11/1992 | Saitoh et al. |
| 5,167,231 A | 12/1992 | Matsui |
| 5,203,336 A | 4/1993 | Iida et al. |
| 5,218,869 A | 6/1993 | Pummer |
| 5,235,986 A | 8/1993 | Maslak et al. |
| 5,391,140 A | 2/1995 | Schaetzle et al. |
| 5,394,877 A | 3/1995 | Orr et al. |
| 5,417,215 A | 5/1995 | Evans et al. |
| 5,435,311 A | 7/1995 | Umemura et al. |
| 5,437,278 A | 8/1995 | Wilk |
| 5,448,994 A | 9/1995 | Iinuma |
| 5,488,952 A | 2/1996 | Schoolman |
| 5,497,776 A | 3/1996 | Yamazaki et al. |
| 5,526,815 A | 6/1996 | Granz et al. |
| 5,611,343 A | 3/1997 | Wilson |
| 5,611,345 A | 3/1997 | Hibbeln |
| 5,619,999 A | 4/1997 | Von Behren et al. |
| 5,666,953 A | 9/1997 | Wilk |
| 5,682,895 A | 11/1997 | Ishiguro |
| 5,752,518 A | 5/1998 | McGee et al. |
| 5,793,701 A | 8/1998 | Wright et al. |
| 5,806,521 A | 9/1998 | Morimoto et al. |
| 5,817,019 A | 10/1998 | Kawashima |
| 5,865,750 A | 2/1999 | Hatfield et al. |
| 5,871,446 A | 2/1999 | Wilk |
| 5,876,342 A | 3/1999 | Chen et al. |
| 5,984,882 A | 11/1999 | Rosenschein et al. |
| 5,997,479 A | 12/1999 | Thiele et al. |
| 6,007,489 A | 12/1999 | Yost et al. |
| 6,013,032 A | 1/2000 | Savord |
| 6,014,897 A * | 1/2000 | Mo | 73/628 |
| 6,023,632 A | 2/2000 | Wilk |
| 6,042,546 A | 3/2000 | Bae |
| 6,059,727 A | 5/2000 | Fowlkes et al. |
| 6,106,463 A | 8/2000 | Wilk |
| 6,106,471 A | 8/2000 | Wiesauer et al. |
| 6,129,672 A | 10/2000 | Seward et al. |
| 6,135,960 A | 10/2000 | Holmberg |
| 6,155,978 A | 12/2000 | Cline et al. |
| 6,213,947 B1 * | 4/2001 | Phillips | 600/443 |
| 6,238,346 B1 | 5/2001 | Mason |
| 6,419,633 B1 | 7/2002 | Robinson et al. |
| 6,436,044 B1 * | 8/2002 | Wang | 600/443 |
| 6,458,083 B1 * | 10/2002 | Jago et al. | 600/443 |
| 6,482,157 B2 * | 11/2002 | Robinson | 600/437 |
| 6,482,160 B1 | 11/2002 | Stergiopoulos et al. |
| 6,494,839 B1 * | 12/2002 | Averkiou | 600/443 |
| 6,503,204 B1 | 1/2003 | Sumanaweera et al. |
| 6,602,194 B2 * | 8/2003 | Roundhill et al. | 600/443 |
| 6,704,438 B1 * | 3/2004 | Alexandru | 382/128 |
| 6,867,720 B1 * | 3/2005 | Freeman et al. | 341/143 |
| 6,980,419 B2 * | 12/2005 | Smith et al. | 361/681 |
| 2002/0035328 A1 * | 3/2002 | Roundhill et al. | 600/443 |
| 2003/0163046 A1 * | 8/2003 | Nohara et al. | 600/443 |

OTHER PUBLICATIONS

Elevation Beamfoaming Performance of a 1.75D Array; by Puyun Guo, Shikui Yan and Quing Zhu; IEEE Ultrasound, Ferroelectronics and Frequency Control, Oct. 2001.

* cited by examiner

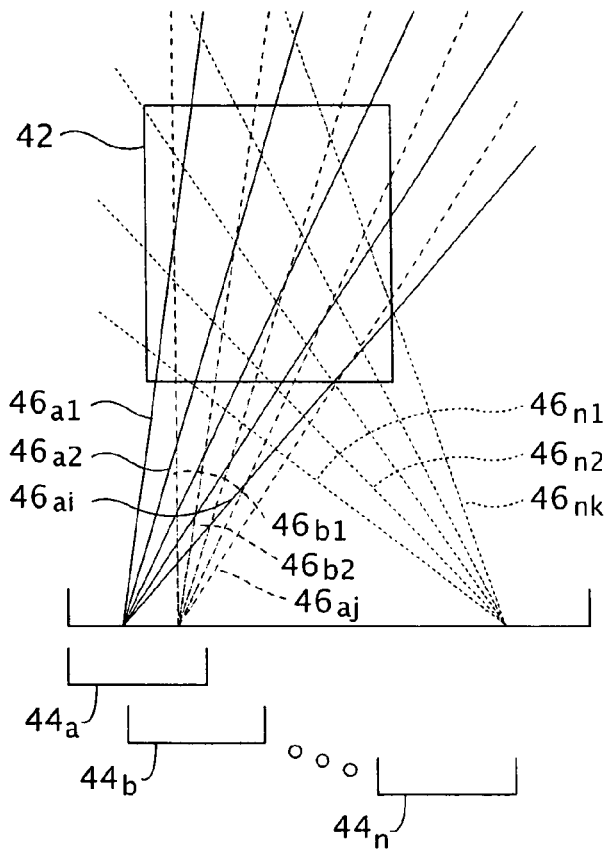
FIG. 2A
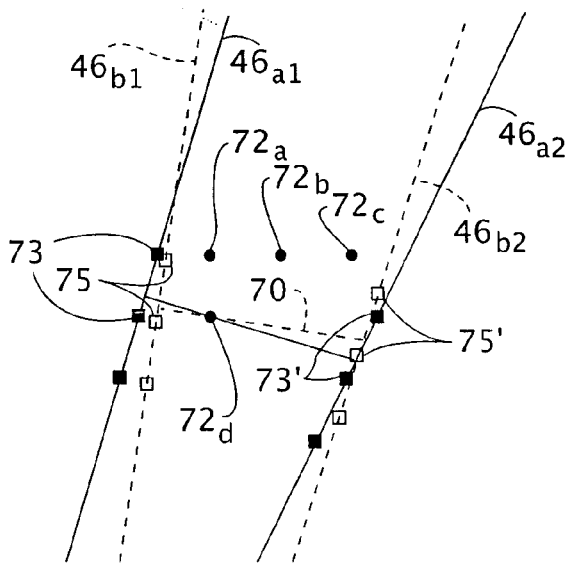
FIG. 2B
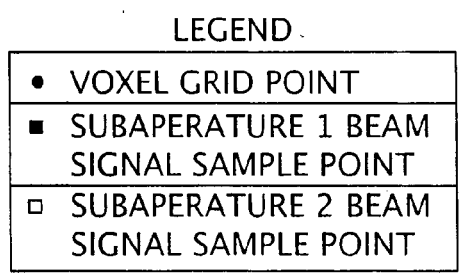

REAL-TIME 3D ULTRASONIC IMAGING APPARATUS AND METHOD

FIELD OF INVENTION

This invention relates to ultrasound imaging systems. More particularly, this invention relates to methods and devices for three-dimensional image acquisition. The devices and methods are also suitable for 2D, 3D and 4D ultrasound systems. The invention is particularly, but not exclusively, useful for medical diagnoses and treatment. The devices and methods of the present invention are useful components of practical high-quality real-time 3D ultrasound systems with fully electronic volume data acquisition.

BACKGROUND OF THE INVENTION

Two-dimensional (2D) ultrasonic probes are necessary to support three-dimensional (3D) electronic, volume data acquisition for many clinical applications. State-of-the-art one-dimensional (1D and 1.5D) probes that electronically scan only in azimuth provide the 2D ultrasound images (azimuth and range) that are commonly used today. 2D probes scan electronically in elevation as well as azimuth, to provide a three-dimensional data cube (azimuth, elevation and range) that can be processed using image processing software to produce a variety of image formats. These formats include conventional planar images, planar images at arbitrary scan planes, as well as representations such as surface rendering and orthographic presentations. Four-dimensional (4D) representations include 3D animations where the 3D rendering is updated in time.

Two-dimensional sensors are employed in other imaging modalities such as CT-scanners, and in other fields such as radar; and hence are well understood conceptually. Practical difficulties arise with the ultrasound modality due to the small, elemental feature size (fractions of a mm) and the large number of channels typically needed. These difficulties have stalled the introduction of fully electronic, 2D, ultrasonic probes.

1D array transducers contain several tens or even hundreds of elements typically arranged linearly. The transducer elements may be arranged on a straight line (linear array) or a curved line (curved linear array or simply curved array). The operations of a linear array or curved array are similar, the main difference being that the image expands with range (depth) for the curved array. A typical linear or curved array could have anywhere from 64 to 512 (or more) elements, depending on the cost and the application. The azimuthal spacing of elements is typically between half a wavelength and one wavelength. The elemental size in the elevation dimension is much larger, typically tens of wavelengths. The operating frequency is typically somewhere between 2 MHz to 20 MHz, depending on the clinical application.

A narrow beam is created in the azimuth dimension by focussing the transmitted and receive energy along a particular beam or scan line. Scanning is performed in azimuth (i.e. in a single elevation plane) using one of two schemes, sequential scanning or phased-array scanning. With sequential scanning, any given beam line is offset from all of the other beam lines in the azimuth direction. If the array is linear (rather than curved), the beam lines are parallel to one another, and a set of beam lines spans the region or volume to be imaged. Phased-array scanning, on the other hand, is achieved by rotating the central beam line in azimuth, to the left and to the right, by a set of angular offsets. The resulting set of beam lines intersect at a common apex (which may actually occur behind the array), and separate from each other as a function of range.

Premium probes generally employ wideband waveforms to achieve the fine resolutions needed in range. As a result, beamforming is done by adjusting time delays (in the narrowband waveform case, phases are adjusted rather than time delays) at each element used on transmit and receive. For a given pulse, a focal point is set along the range dimension. Appropriate time delays are used on the elements involved in transmission, so that their respective acoustic energy arrives at the specified focal range, along the specified beam line, at the same time. As a result, the waveform is said to be focused at this point. On receive, time delays are dynamically applied to the elements involved in reception, to focus the received energy at each range.

The 1.5D array provides a solution to the image thickness problem, and therefore produces higher-quality, planar images than the 1D array (Wildes, D. G., et al., "Elevation Performance of 1.25D and 1.5D Transducer Arrays", IEEE Transactions on Ultrasound, Ferroelectronics and Frequency Control, Vol. 44, No. 5, September 1997, pp. 1027 to 1036). By using multiple rows of elements in the elevation dimension, multiple elevation beams can be formed, each focused at a different focal range. This is achieved by varying the time delays (through switching or otherwise) applied to the elevation elements while the acoustic signals are being received. In addition, a lens is typically used in the elevation dimension to help control the elevation focus. The net effect is that the elevation thickness (resolution) is maintained with range, thereby improving image quality.

Unlike 1.5D arrays which are commonly found in premium ultrasound systems, 1.75D arrays are not yet in use in commercial systems (Puyun Guo, Shikui Yan and Quing Zhu, "Elevation Beamforming Performance of a 1.75D array", IEEE 2001 Ultrasound, Ferroelectronics and Frequency Control Conference). 1.75D arrays are like 1.5D arrays, except there is no symmetry constraint. As a result, it is possible to provide a little bit of elevation steering. However, due to the large element size in elevation (several wavelengths), grating lobes become serious if the electronic scanning is significant.

Interest in 3D Ultrasound is growing and all major ultrasound companies are paying attention. There are two ways that scanning is currently performed: sequential scanning and phased array scanning. It is common knowledge to those skilled in the art that if one conventionally-extends a 1D phased array (typically with λ/2 element spacing) to two dimensions (of equal size), or a 1D sequential array (typically with λ element spacing) to two dimensions, then data cubes could be acquired by 2D scanning, and the fine (e.g. an F number of 2, denoted herein as F/2) azimuth resolution currently available extends to elevation as well. Two fundamental difficulties, however, arise:

1. the cost is prohibitive;
2. the frame-time to acquire a 3D volume is far greater than the time it takes to acquire a 2D image.

Consider extending a linear array with 256 elements (maximum of 128 used on receive) to two dimensions. The number of elements increases to 256×256=65,536. Such a transducer design/fabrication is very difficult, if not impossible, today. The number of receiver channels would also increase by a factor of 128 in order to provide the same resolution in both dimensions, all else being equal, while not increasing the number of shots (and hence acquisition time) needed per vector. Since system cost is proportional to the number of channels, the resulting cost is unaffordable.

Finally, it takes longer to acquire the data cube (as compared to the tens of milliseconds needed to acquire a conventional 2D image plane) since there are many more beams needed to interrogate the volume. At least 128×128=16,384 beams are needed, for each transmit focal range, with about 100 μs two-way time needed for each shot (this assumes a 10 kHz firing rate and a 7 cm depth needed). For two focal ranges, this implies an acquisition time of 3.2 seconds, assuming the number of channels available equals the number of elements used in the beamformer.

The aforementioned difficulties require practical trade-offs and novel solutions if 2D arrays supporting 3D electronic, volume data acquisition are to be an affordable reality.

In U.S. patent application Ser. No. 10/353,152 "3D Ultrasonic Imaging Apparatus and Method", an apparatus and method are disclosed that solve these aforementioned difficulties and provide high-performance, affordable 3D electronic volume acquisition. The apparatus includes a novel 2D probe with 2 different element sizes, a large size in one dimension (normally elevation) and a conventional size in the other (normally azimuth). A new method referred to as coherent aperture combining beamforming (CAC-BF) that can be used in at least one dimension (normally azimuth) with the 2D probe, or on its own, is disclosed. The present application discloses additional improvements to the CAC-BF method that provide image performance enhancements and make the method more flexible and more amenable for real-time implementation.

OBJECTS OF THE INVENTION

An object of the present invention is to provide ultrasound imaging technology which may be incorporated in practical, affordable, high-quality, 3D ultrasound imaging systems which are clinically useful, and which exploit 3D, electronic, volume data acquisition.

Another object of the present invention is to provide 3D ultrasound systems using state-of-the-art elemental transducer technology (e.g. using 1.75D transducer technology), switching, multiplexer and cable technology, and real-time signal processing technology such as ASIC beamforming and filtering hardware.

The most significant cost and complexity in premium 2D ultrasound systems relates to the receive electronics, the cost of which is proportional to the number of digital receive channels. For affordability therefore, another object of the present invention is to keep the number of digital receive channels in the contemplated 3D ultrasound systems similar to that provided in current premium 2D ultrasounds.

A further object of the present invention is that the 2D probe apparatus and beamforming methods disclosed provide high-quality volume data which can be used to generate high-quality 3D imagery (e.g. 3D surface rendering or orthographic presentations) as well as 2D imagery of similar or better quality than premium, state-of-the-art, 2D ultrasound systems currently produce. High-quality imagery is characterized by azimuth, elevation and range resolutions equal to or better than that provided by premium 2D ultrasound systems, as well as grating lobe beam responses (or sidelobe responses for narrowband systems) similar to that provided by premium 2D systems.

It is another object of the present invention to provide azimuth resolution that is significantly better than that of a premium 2D ultrasound system using the same azimuth aperture.

It is another object of the present invention to provide means to produce elevation resolution significantly better than that provided by premium 1.5D arrays in use today.

It is another object of the present invention to provide fully-electronic, 3D volume data acquisition to support rapid and accurate interrogation of volumes combined with highest-quality, 3D image formation.

In order to maximize the clinical utility of the 3D ultrasound system contemplated with the present invention, it is an object of the invention to minimize the 3D volume acquisition time to sustain the highest 3D frame rates without significantly sacrificing affordability or image quality. For example, it is an object of the present invention that meaningful, high-quality 3D data cubes can be electronically acquired in a fraction of one second.

Another object of the present invention is to provide 2D probe and beamforming technology that can be manufactured in a conformal form factor, and be used as a building block (i.e. providing transmission apertures and data gathering apertures) in ultrasound medical imaging systems, exemplarily as described in U.S. Pat. No. 5,666,953, U.S. Pat. No. 5,871,446, U.S. Pat. No. 6,023,632, U.S. Pat. No. 6,319,201, and U.S. Pat. No. 6,106,463.

Another object of the present invention is to provide a compact and deployable 3D ultrasound system of size, weight, power, and form-factor similar to conventional 2D ultrasound systems.

Yet another object of the present invention is to increase the image quality of light-weight, portable, 2D ultrasound imaging systems employing fewer receive channels than premium 2D ultrasounds, without appreciably increasing the size or cost of such improved systems.

Another object of the present invention is to provide an apparatus and method that would support the development of a very low-cost, 2D, real-time ultrasound imaging system requiring only a few (on the order of 8) channels.

Another object of the present invention is to provide an ultrasound system for 3D imaging of the carotid artery, providing improvements in safety and accuracy over current diagnostic methods.

A further object of the present invention is to provide ultrasound technology permitting a standard 2D ultrasound medical procedure to be carried out more quickly and hence more safely.

An additional object of the present invention is to provide ultrasound technology enabling a relatively unskilled medical practitioner the ability to perform an ultrasound medical procedure.

A key object of the present invention is to reduce CAC-BF computation time and latency so that real-time imaging is achieved.

A further object of the invention is to reduce sidelobe levels in all image regions as compared to those levels achieved using CAC-BF or similar methods.

Another object of the invention is to reduce sidelobe levels for ultrasound systems with imperfect hardware.

Another key object of the present invention is to provide a flexible imaging method that is easily programmable for different applications, modes and imaging configurations.

A further object of the present invention is to reduce the latency between shots that are coherently summed, thereby mitigating the effects of tissue motion.

Another object of the present invention is to provide the means to fill-in the near-range holes that can otherwise result in image coverage using CAC-BF or similar methods.

An object of the present invention is to reduce the number of shots transmitted while still achieving desired performance.

Further objects of the invention will be apparent from the drawings and descriptions herein. It is to be noted that each object is achieved by at least one embodiment of the present invention. However, it is not necessary that any given embodiment achieve all of the objects of the invention.

SUMMARY OF THE INVENTION

The present invention addresses the above-mentioned difficulties by employing innovative approaches which together provide a practical solution to ultrasound imaging systems employing 2D ultrasonic arrays which support electronic, 3D volume data acquisition and beamforming.

The present invention is directed in part to a probe for electronic, 3D volume data acquisition using ultrasound, comprising a plurality of transducer elements arranged in a two dimensional array having an azimuth dimension and an elevation dimension. The transducer elements have a first element size in the azimuth dimension and a second element size in the elevation dimension. In a preferred embodiment, at least one of the first and second element sizes is at least twice a characteristic wavelength of a waveform used to drive the array of transducer elements, where the characteristic wavelength is defined as the wavelength corresponding to a center frequency of the waveform.

In a particular embodiment, an ultrasound imaging transducer in a system in accordance with the present invention exploits 1.75D elemental technology (Puyun Guo, Shikui Yan and Quing Zhu, "Elevation Beamforming Performance of a 1.75D array", IEEE 2001 Ultrasound, Ferroelectronics and Frequency Control Conference).

An ultrasound imaging transducer in a system in accordance with the present invention can be manufactured in a conformal form factor, and be used as a building block (i.e., a 2D transducer array module) in ultrasound blanket systems as disclosed in U.S. Pat. No. 5,666,953 and its progeny.

The present invention is also directed to a method of generating image data in a scanning process, using a CAC-BF (see below) technique in at least one of an azimuth dimension and an elevation dimension, to form an ultrasound image line, image plane, or image data cube. The CAC-BF method can be applied advantageously to any 1D or 2D ultrasonic probe or array, and is not restricted to the preferred embodiments disclosed herein.

The present invention includes a beamforming method (CAC-BF) that produces high-resolution ultrasound images more efficiently than conventional methods. CAC-BF divides the transducer into a number of smaller subapertures, each of which transmits and receives a number of low-resolution beams that span the imaged region. High resolution is obtained at each image point by coherently combining the beamformed signals from the subapertures, synthesising a large aperture focussed at the point.

The present invention provides practical, clinically useful, high-resolution, 3D ultrasound, electronic, volume data acquisition.

An ultrasound imaging system in accordance with the present invention exhibits 3D imaging with voxel resolution equal to or better than that of state-of-the-art planar images, in both the azimuth and elevation dimensions. In one preferred embodiment, the voxel resolution is twice as good in azimuth and/or elevation as that in state-of-the-art planar images.

An ultrasound imaging system in accordance with the present invention is relatively inexpensive to manufacture. The imaging system can be implemented as an inexpensive upgrade to existing premium ultrasound systems, or as a stand-alone solution of comparable cost to state-of-the-art 2D ultrasound systems.

In a particular embodiment, an ultrasound system in accordance with the present invention is able to electronically acquire the 3D data cube of size 26 mm×26 mm by 70 mm spanned by the transducer in under one second.

It is obvious to one skilled in the art that there is more to building a 2D or 3D ultrasound imaging system as contemplated herein than simply employing the disclosed 2D arrays or CAC-BF method. The design and implementation of a complete probe, beamformer or ultrasound imaging system assumes a large amount of hardware, software, and systems engineering and manufacturing knowledge known to those skilled in the art. While it is a preferred embodiment of the present invention for the CAC-BF coarse and fine beamforming operations (see description below) to be performed digitally in the ultrasound engine, this functionality can also be distributed throughout the entire ultrasound system, and be implemented in hardware or software or both in a variety of ways known to those skilled in the art, without departing from the scope of the present invention. In addition, post-beamforming operations such as vector processing and imaging processing are also known to those skilled in the art, and any conventional form of these operations could obviously be used effectively with the disclosed inventions. The present disclosure does not provide a tutorial on such techniques, but rather, focuses on the invention itself; namely, the CAC-BF method and its use in ultrasound systems. In particular, the adaptability and flexibility of the CAC-BF method for use in different applications and modes is described. In addition, a shot-machine approach to implementing the CAC-BF method is proposed, which has significant real-time and latency advantages over the simpler frame machine approach. In addition, novel methods are proposed for providing better sidelobe performance, increasing frame rate, reducing latency between coherently summed shots, and filling in near-range blind zones.

The initial target application of the present invention is the carotid artery, although there is nothing that would restrict its use in other applications (e.g. obstetrics and gynecology, abdominal, cardiology, and other peripheral vascular applications). The CAC-BF method which is a key part of the present invention is suitable for use with different sizes and shapes of probes, different numbers of elements in each dimension, and different numbers of channels. It is also suitable for different levels of system cost, i.e. both for low-end systems with only a few channels, and for high-performance imaging systems with hundreds of real channels. The 2D probe which can be advantageously used by the CAC-BF method of the present invention and which fully disclosed in U.S. patent application Ser. No. 10/353,152 (U.S. patent Publication No. 20030163046) is well suited to peripheral vascular applications such as carotid artery imaging. The inventors have developed a real-time prototype of the present invention directed towards carotid artery imaging, and hence, many of the preferred embodiments described herein relate to that application. It will become clear to anyone skilled in the art after reading the present disclosure, that the invention disclosed herein is applicable to any diagnostic ultrasound application.

The present invention is directed at B-mode imaging. However, it is compatible with Doppler modes (both color flow and spectral Doppler modes) and harmonic imaging. Doppler modes using CAC-BF transmit consecutive pairs (or larger groups) of shots in the same direction from the same subaperture. The range lines from each shot pair (or group) are summed and differenced coherently, providing Doppler information. Then CAC-BF integration is applied to the Doppler-combined signals, producing higher-resolution spectral or peak velocity estimates, depending on the Doppler and CAC-BF integration algorithms used. While accounting for the expected target motion, all of the standard CAC-BF configuration parameters described earlier, along with Doppler algorithm and waveform parameters known to those skilled in the art can be optimized to deliver the required spatial resolution. B-mode CAC-BF shots can be interleaved with Doppler shots, where the Doppler shots can use either appropriately configured CAC-BF shots or conventional Doppler shots. Some shots could be used (i.e. shared) by each of the modes. Harmonic imaging can also be supported: in this mode, the waveform (transmission and reception frequencies) is carried out in the usual fashion; however, the transducer elements are controlled (i.e. excited and received) in accordance with the CAC-BF method. The peak power and CAC-BF subaperture configuration employed (e.g. size, spacing, overlap) are optimized so that the harmonic component is excited in the tissue being imaged.

The CAC-BF method of the present invention supports a shot machine approach to processing received ultrasonic signals which makes the CAC-BF algorithm particularly flexible and amenable to real-time operation. With a shot-machine, the ultrasound signals received from a given transmitted shot are processed immediately and make their contribution to the resulting acquired image data; the next shot is then fired and the process repeats itself until the entire image is formed. A frame machine, on the other hand, would typically collect and store ultrasound signals from the set of shots associated with an image frame. One or more processing steps would be a block process that would require all of the ultrasound signals for a given frame to be available to operate on. This introduces latencies and is in general less computationally efficient than a shot machine implementation. A shot machine implementation, however, is typically more difficult to design as the algorithmic steps are reorganized, combined and optimized to achieve efficiency.

In accordance with the present invention, the spatial and temporal interpolations used during scan conversion, the aperture windowing used for sidelobe control, and the calibrated equalization process are all combined into a minimal set of multiplying weights to minimize the number of CAC-BF computations. In a preferred embodiment, these weights are pre-computed and stored along with corresponding memory addresses in order to minimize the number of CAC-BF computations and the resulting on-line computation time.

The invention proposes a number of aperture windowing and calibration methods to improve the azimuth sidelobes in the CAC-BF impulse response. With an unweighted CAC-BF summation across the subapertures, higher azimuth sidelobes (Fresnel ripples) result. Specialized windowing (weighting) methods suitable for use with CAC-BF provide part of the solution. However, if the system hardware response between different shots is unequal in gain and phase, then windowing by itself is not effective. Thus real systems need calibration and equalization.

Due to the shot machine architecture, arbitrary ordering of shots is possible. Methods are proposed for ordering the shots used by the CAC-BF algorithm that reduce the latency between those that are summed together. If shots are simply ordered by aperture or by beam angle, then some regions of the image can have unacceptably long time between the shots used in their specific CAC-BF summation. Also, a method is proposed for shot selection for the CAC-BF algorithm that adds extra shots to cover the short-range.

The CAC-BF method associated with the present invention is also parameterized to make the method programmable for different modes and CAC-BF configurations. This allows it to be used in more systems and applications, and is quite amenable to a software machine. For upgrades to existing machines, the method is well suited to exploiting beamforming and focusing hardware already available for the coarse beamforming step, and performing the fine beamforming step in software. For such a case, the methods described herein have been implemented in software in real-time on off-the-shelf personal computers.

COMPARISON OF INVENTION WITH PRIOR ART

In U.S. Pat. No. 4,553,437 "Hybrid Non-Invasive Ultrasonic Imaging System", Luthra, Kassam and Mauchly describe a method referred to as complex image addition (CIA) for use with a linear array that has similarities with the CAC-BF method. In addition, they also describe an apparatus that consists of a linear array, and a frame machine circuit that implements the CIA method. The CIA method has several shortcomings as compared to the CAC-BF method disclosed herein. First, the CIA method only works with a linear array, whereas the CAC-BF method works for any array, and hence is applicable to both 2D imaging, as well as 3D imaging. The '437 patent does not deal with azimuth sidelobe control and aperture weighting. Nearest neighbour selection rather than azimuth and/or range interpolation are used during scan conversion in '437, owing to the complexities of their frame machine, and the large subapertures (64 elements) used. Interpolation processes proposed herein are more accurate than the nearest neighbour (in both dimensions) approach in the '437 patent and are necessary for the smaller subapertures favoured in the preferred embodiments of the CAC-BF method. The '437 patent has exactly a 50% overlap between subapertures and does not teach that overlap is important for eliminating grating lobes. Calibration is not dealt with in the '437 patent, and shot ordering algorithms to reduce latency are not conceived. Additional differences between the '437 patent and the present invention are described below.

The '437 patent's method/apparatus or approach is a frame machine approach, i.e. all shots are fired and stored before being processed using complex image addition to generate the final image. This approach introduces latencies, and requires storage for all acquired samples. With the shot machine approach of the present invention, each shot makes an immediate contribution to the image so that latencies are minimized.

Our invention features easy to use, user-selectable, on-the-fly, configuration changes to CAC-BF imaging parameters. The '437 patent discloses a method and apparatus that are rigid and not amenable to such changes. The present invention is amenable to a turn the knob concept of trading off image resolution, image size, frame rate, and image quality; and this is a novel feature of the present invention not taught by the '437 patent. The present invention includes a software, programmable, low-cost implementation as a preferred embodiment that is already proven in the form of a prototype.

In the '437 patent, each subaperture uses the same set of scan lines. In our invention, each subaperture need not use the same set of scan lines. For example, the subapertures on the edges of the total aperture need not scan outside of the desired image limits. In this way, the present invention minimizes frame time.

In the '437 patent, the acquired image field of view is that able to be seen by all subapertures, i.e. each point in the image includes a complex sample acquired from each subaperture.

Our approach is more flexible. We can emulate sector image formats and linear scan formats just by a change in parameters.

With our approach, we can use CAC-BF for some image regions and conventional beamforming for others. This flexibility is useful when using certain CAC-BF configurations, for example, a linear scan format, where near-range 'holes' or blind zones in CAC-BF coverage can result. For such cases, a few extra conventional shots can be fired to fill in the holes as necessary.

The '437 patent is directed towards relatively large subapertures (64 elements) as compared to the total aperture (128 elements) that gets utilized (even though they refer to their subapertures as being small). The present CAC-BF invention is directed to very small subapertures (i.e. 8 or 16 as compared to the 128 total utilized aperture). We are directed to smaller subapertures for two reasons: i. they support low-cost 2D machines with only 8 or 16 channels; and ii. they support 64 or 128 channel 3D machines. The larger subapertures used in the '437 patent have high gain and small depth of focus. Therefore they prefer to transmit on half the aperture (and consequently lose SNR and introduce imaging artifacts) to get suitable depth of focus (DOF). Our approach of using small subapertures means we get greater DOF by definition. Hence we transmit and receive on the same subaperture and improve imaging properties.

The '437 patent does not teach the savings in frame time achievable using CAC-BF. CAC-BF requires a constant number of shots (and hence frame time) independent of size of the subaperture. Hence the frame time can be held constant while the subaperture size is selected to match the system front end (i.e. number of channels) specification. This is highly advantageous. Our CAC-BF method is also very advantageous in number of shots compared to the standard synthetic aperture approach.

Another benefit of CAC-BF is that it gets twice the resolution of conventional methods using a total aperture of the same size. The CIA method taught by '437 patent does not teach this. Also, because it uses only one-half of its subaperture during transmission, the CIA method will have significant grating lobes.

In Ultrasonic Blanket with CAC and SCA Patent Application, U.S. Ser. No. 09/514,928, filed 28 Feb. 2000, 3D volume data acquisition and focusing of beams using active transducers is described. A singular, rigid carrier structure constructed using scalar transducer elements arranged in the likeness of an array is disclosed. Signal transmission apertures and data gathering apertures are formed and used to electronically scan desired regions and electronically acquire 3D volumetric data; where coherent aperture combining (CAC) is used to combine the structural data from multiple data gathering apertures, thereby increasing the size of the effective data gathering apertures employed, and thereby increasing image resolution. Both monostatic (on pulse one, transmit and receive out of aperture one, on pulse two, transmit and receive out of aperture two) and bistatic (transmit from one aperture and receive simultaneously on two or more apertures) operations are disclosed. Also disclosed is the use of 1.5D and 1.75D array technology to form a 2D array and effectuate volume data acquisition by scanning in azimuth and elevation. The 2D carotid probe described herein is a particular apparatus in the form of a 2D array that uses elements that are larger in one dimension (e.g. elevation) than the one (e.g. azimuth) as 1.5D and 1.75D linear arrays employ, but which is designed particularly for carotid or peripheral vascular imaging. The CAC-BF method of the present invention is a major advancement over the CAC method, and discloses numerous algorithm steps and details that are simply not considered by the aforementioned CAC method.

In U.S. patent application Ser. No. 10/353,152 "3D Ultrasonic Imaging Apparatus and Method" (U.S. patent Publication No. 20030163046), the 2D carotid probe described herein was first disclosed. The CAC-BF method teaches several improvements over the earlier method described in the aforementioned application. These improvements relate to a shot-machine implementation of CAC-BF, particular aperture windowing algorithms and calibration procedures for sidelobe control, extension to other applications and modes, filling in of short-range holes or blind zones using conventional shots, and special shot-ordering methods that minimize acquisition latencies.

BRIEF DESCRIPTION OF THE DRAWINGS

FIGS. 2A and 2B are a diagram illustrating basic CAC-BF concepts utilized in carrying out the present invention.

DEFINITIONS

Figure 1:
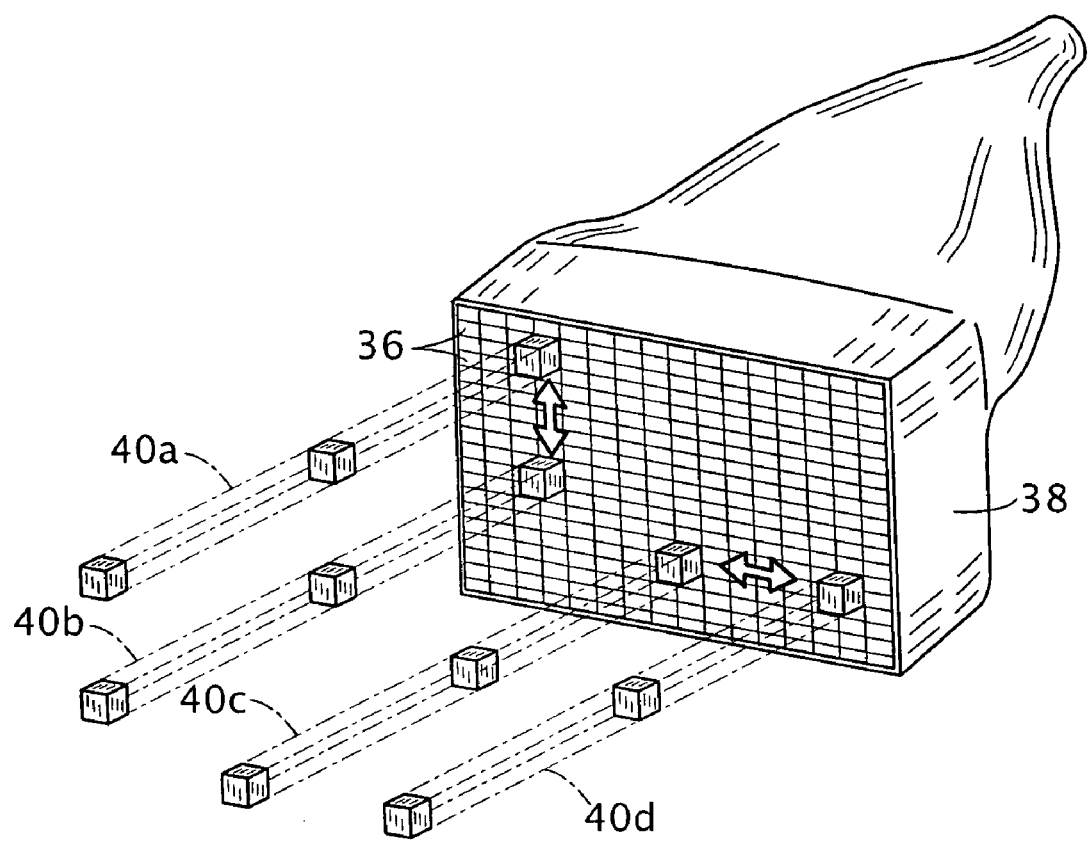
FIG. 1 is a schematic perspective view of a 2D ultrasonic transducer array pursuant to the present invention.

The word "shot" is used broadly herein to refer to a transmission of acoustic energy. The acoustic energy may take the form of a pulse having a center frequency, amplitude and shape.

The word "echo" is used herein to refer to reflected acoustic energy generated when a shot interacts with an internal tissue structure. A particular shot directed along a transmission path will typically generate echoes from all internal body tissue structures along that path. The echoes are reflected back to the receiving aperture or subaperture.

The word "subaperture" as used herein denotes a subset of an available aperture used for spatially directing a shot and/or receiving echoes. When formed from an array of electrical-mechanical transducer elements of an ultrasonic scanner, the transducers of a subaperture are typically contiguous and disposed in a one- or two-dimensional array.

The word "voxel" is used herein to denote a smallest unit of volume to be assigned a respective image value in an ultrasound-generated image. A voxel is a three-dimensional region analogous to a pixel of a two-dimensional image. In general, the image value may take the form of a scalar (e.g.

amplitude or intensity level), a complex quantity (e.g. amplitude and phase), or a vector (e.g. intensity level and velocity).

The term "range line" as used herein refers to a set of echo values received along a particular reception path. For phased arrays, the subaperture transducer signals associated with respective received echoes are weighted and summed by a beamformer to form the range line for a particular reception path. The set of echo values generally correspond to the structures disposed along the reception path.

The term "shot machine" as used herein describes the architecture of an ultrasound system whose underlying design involves the firing of a shot followed by the reception and processing of its respective echoes for a particular range line, followed by making contributions to an image for the tissue structures associated with the particular range line. An entire image is formed by repeating the process for a sequence of shots and associated range lines. Shot machines are inherently flexible and typically can be easily reprogrammed to support different image formats and modes by simply defining a suitable sequence of shots and associated range lines to use.

The term "CAC-BF technique" as used herein refers to a method for forming ultrasound images by (1) transmitting a set of coarse beams in sequence using a set of subapertures, receiving respective echoes from each coarse beam and performing coarse beamforming to form a range line for each coarse beam and (2) coherently combining the received range lines using a fine beamforming process in order to form a high-resolution image. The acronym "CAC-BF" stands for "Coherent Aperture Combining-BeamFormer."

The term "coherent image data" as used herein denotes image data that includes amplitude and phase information, typically represented as a complex quantity for each datum.

The term "complex coherent image" as used herein denotes an image that includes amplitude and phase information at each pixel or voxel, typically represented as a complex quantity at each pixel or voxel.

The term "coarse beam" refers herein to a real beam in a certain direction formed by the transmission of a shot from a subaperture. A coarse beam is usually of lower-resolution (spatially coarser) than the image data synthesized by the CAC-BF technique.

The term "coarse beamforming" refers herein to the process of forming a range line by combining the acoustic signals received from each of the elements of a receiving subaperture.

The term "fine beam" is used herein to designate a synthesised beam formed by the coherent combination of the range lines received from multiple shots and multiple subapertures. A synthesized fine beam usually has higher-resolution (fine) than the coarse beams associated with each of the range lines.

The term "fine beamforming" denotes herein the process of synthesising the higher-resolution (fine) image data, not necessarily as a set of distinct "fine beams", by the coherent combination of range lines formed by coarse beamforming.

A "sample" as that word is used herein means a number in an ordered sequence of digitized data comprising a range line.

The term "aperture windowing" as used herein denotes the beamforming process of assigning smaller multiplicative weighting to signals from the edges of the aperture used. Windowing can reduce sidelobes in the image, at the cost of degrading resolution. Windowing can be applied to full apertures (conventional beamforming), subapertures (e.g. with coarse beamforming), as well as to synthesized apertures (e.g. associated with fine beamforming).

The word "equalization" as in "shot-to-shot equalization" refers herein to the process of (a) measuring inequalities in relative amplitude and phase responses between shots owing to different hardware imperfections in the formation of the respective range lines, and (b) compensating for the inequalities during processing. The inequalities, if not compensated, can lead to both poor focusing and high sidelobes in the image.

The term "coherent image addresses" denotes herein computer memory addresses for each complex voxel in the image being formed (in memory) by CAC-BF.

The term "complex convolution kernel" as used herein refers to a small (e.g., length-20 or so) sequence of complex numbers. This sequence is digitally convolved with each received range line in order to perform the range filtering operation.

The term "short-range blind zone" is used herein to designate regions between subaperture centers that are not illuminated by CAC-BF coarse beams. In a typical CAC-BF configuration, subapertures are spaced by dx (mm), and are used in the transmission of coarse beams that span plus or minus daz (degrees) from normal. The typical, isoceles triangular-shaped regions between subaperture centers, with base lengths dx along the aperture, and sides with internal angles 90-daz, are not illuminated by the CAC-BF coarse beams.

DETAILED DESCRIPTION OF THE PREFERRED EMBODIMENTS

FIG. 1 shows an ultrasound transducer probe where scanning occurs in both the azimuth dimension (i.e. horizontally) and in the elevation dimension (vertically). The probe includes a rectangular array of transducer elements 36 mounted to a holder or substrate member 38. Four different beams 40a, 40b, 40c, 40d are illustrated in FIG. 1, demonstrating that the probe is capable of illuminating a volume. The transducer elements 36 can be controlled to effect sequential scanning in azimuth and elevation as illustrated in FIG. 1; but nothing prevents one from using phased-array scanning or CAC-BF (coherent aperture combining beamforming) scanning (see below) in azimuth and/or elevation. If phased array scanning is used in a given dimension, the acquired data usually is scan converted (i.e. transformed or mapped onto a Cartesian grid) in order to present the image on a conventional display (i.e. a monitor using a cathode ray tube (CRT)). The net effect of any of these scanning techniques is that a volume of ultrasound data is ultimately acquired electronically, which ultimately can be represented on a Cartesian (x-y-z) grid.

A preferred embodiment of the ultrasound transducer device or probe of FIG. 1 for 3D imaging of the carotid artery is described in U.S. patent application Ser. No. 10/353,152 (U.S. patent Publication No. 20030163046) and is characterized by the following baseline parameters:

256×40 piezoelectric transducer elements 36

0.2 mm ($\lambda$)×0.8 mm (4$\lambda$) element spacing in azimuth and elevation, respectively Scans in azimuth and elevation Uses 128-elements for azimuth instantaneous aperture Uses 20% elevation instantaneous aperture (i.e. 8-element subaperture)

TX focal depth is 50 mm

Imaging depth is typically 0 to 7 cm

Nominal azimuth resolution of F/2

Nominal elevation resolution (using 8 elevation elements per beam) of F/8

High elevation resolution (using 16 elevation elements per beam) of F/4

Frequency 7.5 MHz (central wavelength 0.2 mm)

Pulse length 0.4 mm (0.27 µs) with Hann weighting, yielding approximately 100% bandwidth 128 digital receive channels image volume 25.6 mm×25.6 mm×70 mm It should be noted that any of the above parameters, including the frequency, can be changed for other applications in order to create other preferred embodiments, and such changes would not depart from the spirit or scope of the probe in accordance with the present invention.

The aforementioned 2D transducer device of FIG. 1 has several advantages over the conventional 2D array described earlier. The conventional 2D array requires at least four times the number of elements to scan the same volume (assuming the azimuth and elevation element sizes are both λ). If a conventional probe restricts itself to the same number of elements as the 2D transducer device disclosed herein, then it will also result in lower spatial resolution and image quality because the physical aperture will be smaller. As a result, the 2D transducer device is more practical, less complex and less expensive than a similarly performing conventional 2D array.

Figure 7:
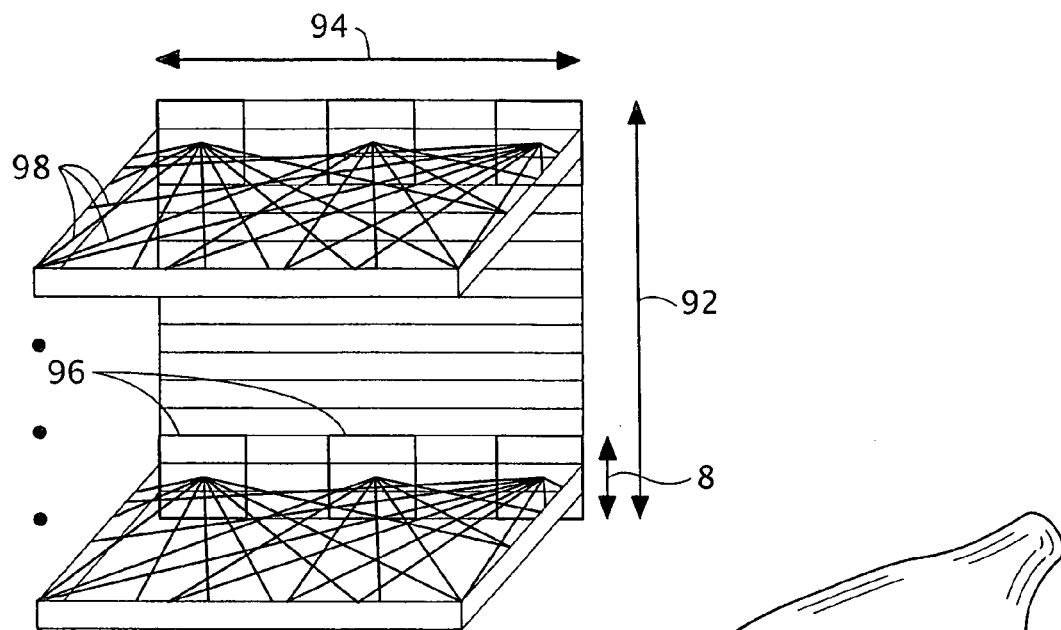
FIG. 7 is a schematic perspective view of a 2D ultrasonic transducer array pursuant to the present invention showing CAC-BF applied in the azimuth dimension and conventional sequential scanning in the elevation dimension. This transducer and scanning approach is well-suited to the carotid artery or other peripheral vascular applications.
Figure 8:
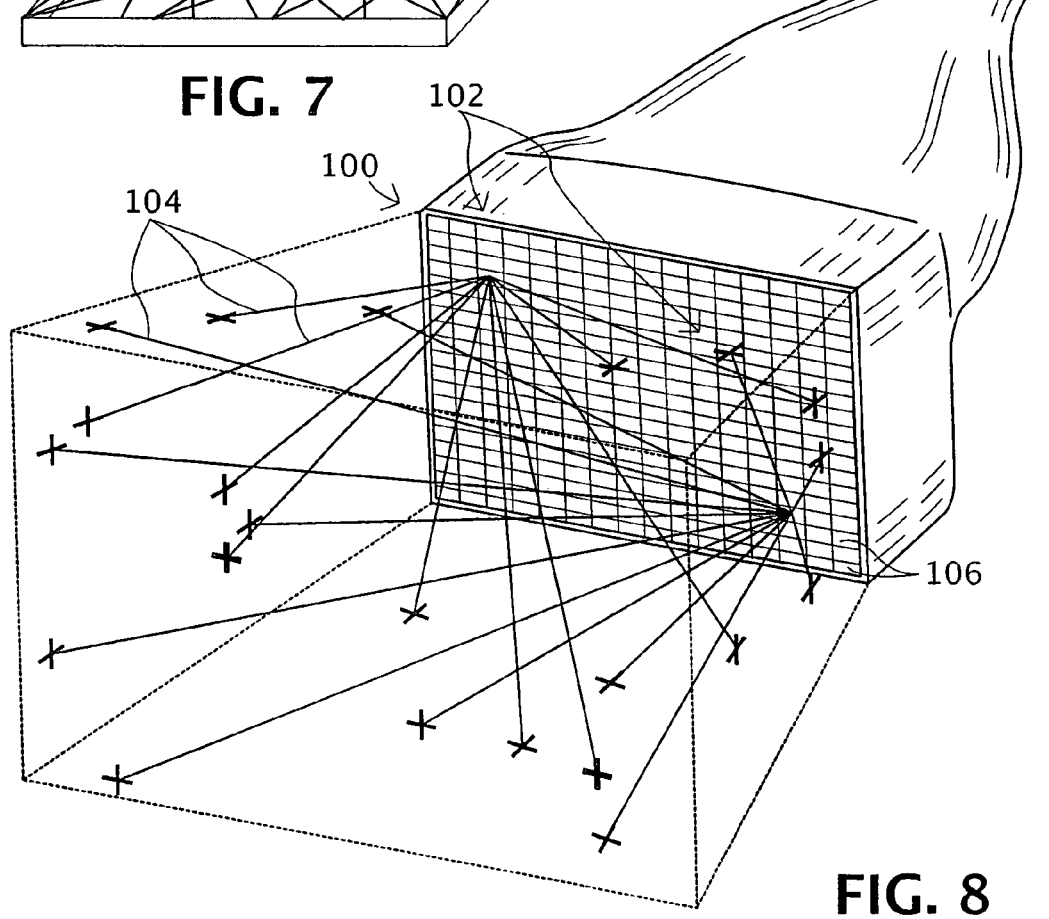
FIG. 8 is a schematic perspective view of a 2D ultrasonic transducer array pursuant to the present invention showing CAC-BF applied in both the azimuth dimension and elevation dimension. This transducer and scanning approach is well-suited for cardiology applications.

CAC-BF scanning, discussed in detail below, can be used with the probe of FIG. 1, or any other 1D or 2D probe, when it is necessary to minimize the volumetric or image acquisition time. When used with the array of FIG. 1, a preferred embodiment of the CAC-BF method uses sequential scanning in elevation 92, combined with CAC-BF in azimuth 94 as illustrated in FIG. 7. In this configuration, 3D imaging can be achieved effectively with as few as 64 channels. For this case, the CAC-BF subapertures 96 are typically of dimension $8_{az}8_{el}$ (i.e. each subaperture has 8 contiguous elements in azimuth and 8 in elevation for a total of 64), and adjacent azimuth' subapertures typically have an overlap of 4 azimuth elements. Typically 8 to 10 phased-array type beams 98 are formed for each subaperture 96 to achieve F/2 in azimuth, and the collection of resulting beams from all subapertures are coherently combined to produce the final image. For abdominal applications, a probe similar to that employed in FIG. 1 could be used, albeit typically at lower frequencies. For cardiology applications, a more conventional 2D array 100 can be used and scanned as shown in FIG. 8. Here, the subapertures 102 also span two dimensions (e.g. 8×8 for a 64 channel systems or 16×16 for a 256 channel system) and phased-array type beams 104 scan in both azimuth and elevation. Subapertures would typically overlap 50% in each dimension and the number of beams 106 used with each subaperture is typically on the order of the number of elements 106 in the subaperture (i.e. 64 beams for an 8×8 subaperture) to achieve good performance. For a given application, the size and number of the subapertures, their overlap, and the number and spacing of beams formed per subaperture are optimized to yield the required performance.

Coherent Aperture Combining Beamforming

In General

The general concept underlying CAC-BF will now be described with reference to FIG. 2A. While this figure pertains to a 1D array for ease of illustration, it is clear by the previous discussion and by reference to FIG. 8 that it extends easily to a 2D array. A volume 42 to be imaged is divided into a Cartesian grid of points (voxels), nominally separated by the achievable resolution in each dimension. A number of subapertures $44_a, 44_b, \ldots 44_n$ are defined within the ultrasound transducer device or probe. A number of beams $46_{a1}, 46_{a2}, \ldots 46_{ai}, 46_{b1}, 46_{b2}, \ldots 46_{bj}, \ldots 46_{n1}, 46_{n2}, \ldots 46_{nk}$ from each subaperture $44_a, 44_b, \ldots 44_n$ are directed towards different angles spanning the volume of interest 42. High-resolution voxels are formed by summing signals from a number of low-resolution (coarse) beams originating from different subapertures $44_a, 44_b, \ldots 44_n$. High resolution is achieved because the summation results in the full aperture (i.e. the total extent of the subapertures) being synthesized and focused at each voxel in the image.

The differences between a method and apparatus using conventional techniques and a method and apparatus utilizing CAC-BF are as follows. Conventional techniques are organized into two categories: those using synthetic aperture beam formation, and those not. We consider the latter first. In a conventional ultrasound (without synthetic aperture beam formation), beams are fully formed, both on transmit and receive, with a single shot. The number of elements in the aperture is thus limited by how many channels are available. The transmit aperture is restricted to be smaller than the receive subaperture to provide a reasonable depth of focus. This means that with the receive hardware currently available (i.e. we do not want to increase the number of receive channels in premium 2D ultrasound systems), high-resolution 2D electronic scanning is not practical. The CAC-BF method differs from high-resolution conventional beamforming in two key ways. First, conventional beamformers do not use subapertures $44_a, 44_b, \ldots 44_n$ in the beamforming process. Second, conventional beamformers transmit on a smaller aperture than they receive on.

In conventional systems with 'synthetic aperture' beamforming, a number of subapertures (offset in azimuth only) are focused along a given range line on consecutive shots, and then the return signals are summed in order to synthesize a single beam. If a high-resolution transmit beam is also needed, then multiple subapertures are used on transmit for each receive subaperture; shots that have different transmit and receive subapertures are 'cross-terms' in the summation. Current premium ultrasounds, when operating in synthetic aperture mode, typically use only two subapertures on receive (There is usually one direct transmit/receive and one cross-term transmit/receive. For example, transmit on a central subaperture and receive on central subaperture, followed by transmit on central and receive on outer subaperture.). Several key differences exist between the CAC-BF method and synthetic aperture beamforming. First, there are no cross-terms in the baseline CAC-BF concept as used herein, meaning that resolution is better for CAC-BF. (With CAC-BF, cross-terms actually decrease resolution, but do help to reduce sidelobes.) Furthermore, CAC-BF uses a small aperture on transmit instead of the larger apertures needed by conventional synthetic aperture methods designed to achieve the same performance. Second, whereas synthetic aperture beamformers form a single high-resolution beam for each voxel, the CAC-BF method forms several coarse, low-resolution beams and combines them at each voxel. Third, in a preferred embodiment of CAC-BF, each low-resolution beam is formed using transmit and receive subapertures that are the same size. In synthetic aperture beamforming, the transmit and receive subapertures used for beam formation are different in size, the transmit being smaller.

In a given region, the CAC-BF concept contemplates that each low-resolution beam is transmitted and received from the same (sub)aperture. High-resolution 'beams' are not really formed; rather a high-resolution aperture is synthesized at each voxel. Multiple low-resolution beams from each sub-aperture cover a region spanning many beamwidths. The ultrasound imaging process utilizing CAC-BF breaks up the existing large aperture.

A conventional ultrasound typically transmits multiple shots to get better depth of field (one shot for each range interval). This is because the transmit beam must be focussed at a particular range, and only voxels for ranges within its depth of focus can use the beam. To cover a wide range swath, a sequence of shots are transmitted along each range line, each focused at a different range. This forces the system to take significantly more time to cover the volume. The higher the resolution, the smaller is the depth of focus, and hence the longer it takes to image a volume. This is also the case for the Complex Image Addition method disclosed in U.S. Pat. No. 4,553,437 where 64-element subapertures are preferred. With the disclosed CAC-BF method, the depth of focus is defined by the resolution of the coarse beams, giving it a natural advantage over state-of-the-art beamforming methods. This is a fundamental difference between conventional beamforming methods and the CAC-BF method. The preferred embodiments of the CAC-BF described herein only require a single shot per range line or image vector.

The ultrasound transducer device (see FIG. 1) is divided or partitioned into overlapping subapertures $44_a$, $44_b$, ... $44_n$ (FIG. 2A). These are composed of (say) 64 to 128 elements to match the available number of signal receive channels. In a preferred embodiment, the subapertures $44_a$, $44_b$, ... $44_n$ overlap by at least 50% of their width in each dimension (azimuth or elevation) where CAC-BF is applied. The percentage overlap strongly affects the impulse response of the resulting, high-resolution, CAC-BF image. Grating lobes may result if not enough overlap is selected. FIG. 2A shows a 1D array partitioned along the azimuth dimension into subapertures $44_a$, $44_b$, ... $44_n$. CAC-BF is illustrated below for this single azimuth dimension. Extension of CAC-BF applied to two dimensions (i.e. azimuth and elevation) is straightforward.

Coherent Aperture Combining Beamforming

Image Partition

The image space 42 is covered by overlapping beams $46_{a1}$, $46_{a2}$, ... $46_{ai}$, $46_{b1}$, $46_{b2}$, ... $46_{bj}$, ... $46_{n1}$, $46_{n2}$, ... $46_{nk}$ from subapertures $44_a$, $44_b$, ... $44_n$. FIG. 2A shows the beam boresights as lines originating from the subapertures $44_a$, $44_b$, ... $44_n$, and travelling through the volume 42. Each subaperture $44_a$, $44_b$, ... $44_n$ transmits and receives a respective sequence of overlapping (coarse) phased-array beams $46_{a1}$, $46_{a2}$, ... $46_{ai}$, $46_{b1}$, $46_{b2}$, ... $46_{bj}$, ... $46_{n1}$, $46_{n2}$, ... $46_{nk}$, each beam being focused at a different angle. A pulse (shot) is transmitted and a range line is received for each beam $46_{a1}$, $46_{a2}$, ... $46_{ai}$, $46_{b1}$, $46_{b2}$, ... $46_{bj}$, ... $46_{n1}$, $46_{n2}$, ... $46_{nk}$ from each subaperture $44_a$, $44_b$, ... $44_n$. The beams for each subaperture are normally spaced so that they cross at approximately their −3 dB points. To avoid grating lobes, the total angle (volume) spanned by the beams $46_{a1}$, $46_{a2}$, ... $46_{ai}$, $46_{b1}$, $46_{b2}$, ... $46_{bj}$, ... $46_{n1}$, $46_{n2}$, ... $46_{nk}$ from each subaperture $44_a$, $44_b$, ... $44_n$ is usually limited by the reciprocal of the element spacing weighted by a constant that takes into account unit conversion. This consequently limits the size of the full aperture that can be synthesized. Only beams that intersect the imaged volume 42 need be transmitted, thereby saving additional acquisition time; thus subapertures at the edges of the volume transmit fewer beams.

Coherent Aperture Combining Beamforming

Image Formation

Figure 3:
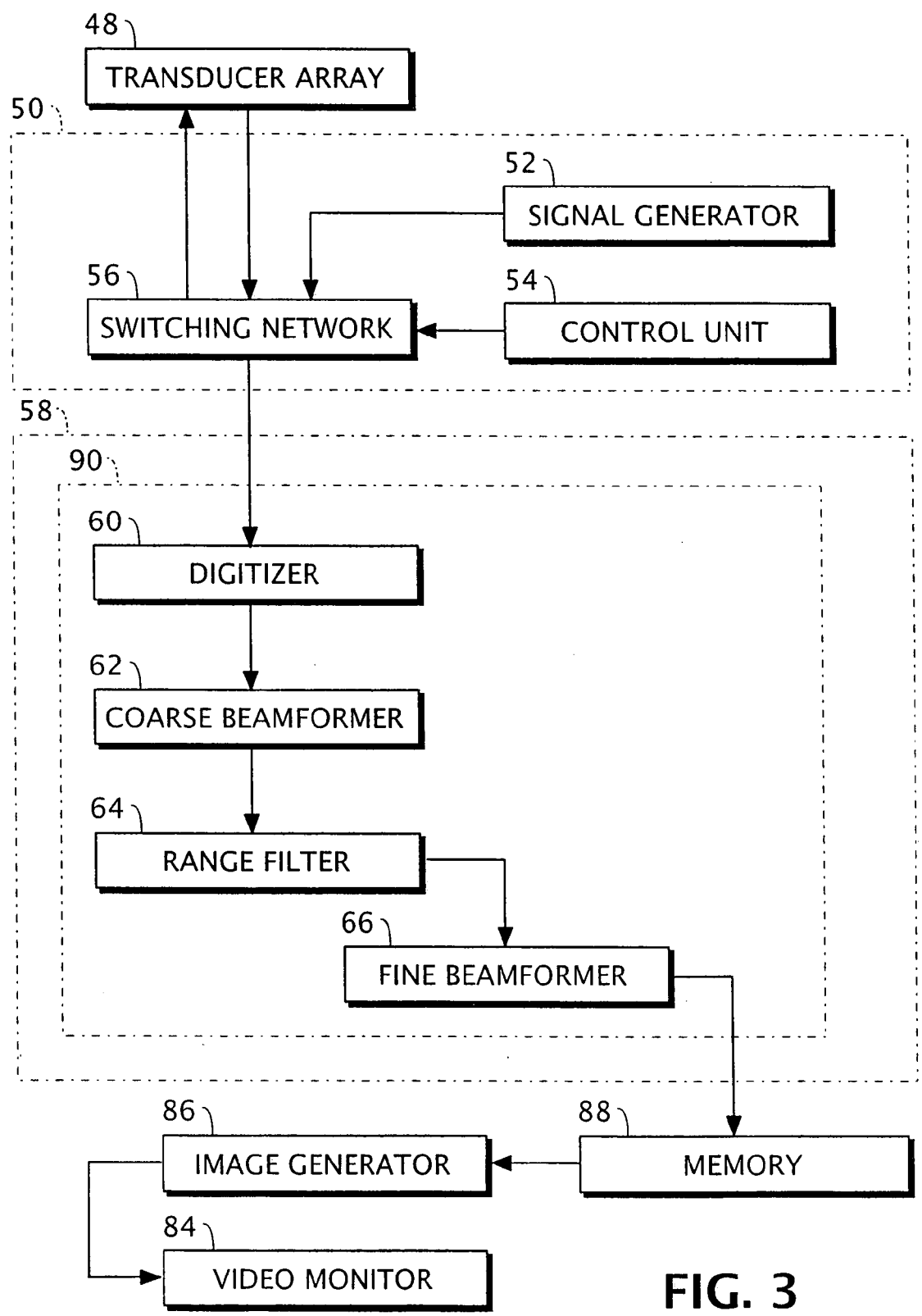
FIG. 3 is a block diagram showing functional components of an ultrasound scanning system in accordance with the present invention.

As illustrated in FIG. 3, a two-dimensional array 48 of transducer elements mounted to a probe (not shown in FIG. 3) is accessed by switching electronics 50. Switching electronics 50 includes a signal generator 52, a control unit 54 and a switching network 56. Signal generator 52 produces a waveform having a characteristic ultrasound frequency that is directed to elements of transducer array 48 by switching network 56 in response to signals from control unit 54. Switching electronics 50 selectively energizes the elements of array 48 and selectively polls those elements to effectively divide the array, along at least one of two dimensions, into subapertures $44_a$, $44_b$, ... $44_n$. As discussed above, each subaperture $44_a$, $44_b$, ... $44_n$ transmits and receives a respective plurality of low-resolution ultrasound beams $46_{a1}$, $46_{a2}$, ... $46_{ai}$, $46_{b1}$, $46_{b2}$, ... $46_{bj}$, ... $46_{n1}$, $46_{n2}$, ... $46_{nk}$ that span the volume 42 to be imaged. A signal processor 58 is operatively coupled to the switching electronics 50 for coherently combining received beamformed signals from the subapertures $44_a$, $44_b$, ... $44_n$, and synthesizing, from the coherent combination, a large aperture focused at each point of the image volume 42.

The image formation process loops on beams $46_{a1}$, $46_{a2}$, ... $46_{ai}$, $46_{b1}$, $46_{b2}$, ... $46_{bj}$, ... $46_{n1}$, $46_{n2}$, ... $46_{nk}$ and subapertures $44_a$, $44_b$, ... $44_n$ (2 nested loops), collecting range lines (the sampled signal in range). From each shot, return signals are received from the transducer elements of the transmitting/receiving subaperture $44_a$, $44_b$, ... $44_n$. These signals are digitized by a digitizer 60 (FIG. 3) and (coarse) beamformed by a module 62, with dynamic focusing along the radial line from the phase center of the subaperture through the transmit focal point, as is usually done.

In this preferred embodiment, the next operation performed on each line is range filtering, performed by a range filter 64. This operation is linear for the fine beamforming step to work optimally, and it retains the phase of the signal; i.e. the output is typically complex (I and Q). A conventional bandpass filter can be applied (matching or exceeding the waveform bandwidth), or alternatively, a matched filter can be used and applied to the ultrasound signals; in this case, a preferred approach is to base the matched filter on the pulse replica (as the real part of the kernel) and its Hilbert transform (as the imaginary part). Range filtering with the transmit pulse is logically done after coarse beamforming, but before fine beamforming, since fine beamforming (module 66) removes the range lines. Range filtering may also be omitted depending on the waveform used.

One advantage of the way coarse beamforming and range filtering is performed is that a 2D ultrasound engine could be used for these operations, making the preferred 2D probe and the CAC-BF method amenable for upgrading existing premium ultrasound systems to 3D.

The resulting coarse beams are transferred to the fine beamforming module 66. Coarse beamformer module 62 and fine beamformer module 66 may be realized by generic digital processor circuits modified by respective programming algorithms to accomplish the respective beamforming operations.

A conventional ultrasound also loops on beams in a similar manner, but our invention uses a unique set of different beams, differing in both the elements used and the focused directions. With conventional ultrasound, each image point is typically generated from the nearest high-resolution beam which is generated from one or more shots. With the CAC-BF method on the other hand, each image point is generated from an associated set of nearby low-resolution beams, each generated from an associated shot.

Images (2D or 3D) may be generated on a video monitor 84 (FIG. 3) by an image generator 86 in response to image data stored in a memory 88 connected to output of processor 58, more particularly to an output of a CAC-BF component 90, and even more particularly to an output of fine beamformer 66. CAC-BF component 90 includes digitizer 60, coarse beamformer 62, range filter 64 and fine beamformer 66.

Coherent Aperture Combining Beamforming

Fine Beamforming

Figure 4:
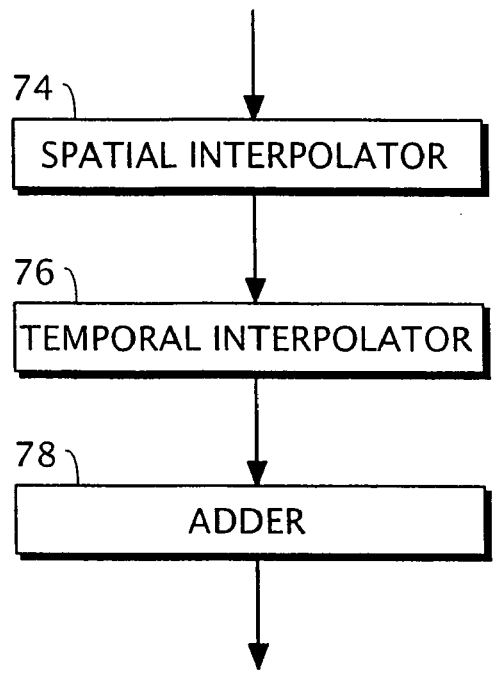
FIG. 4 is a block diagram showing elements of a fine beamformer shown in FIG. 3.
Figure 5:
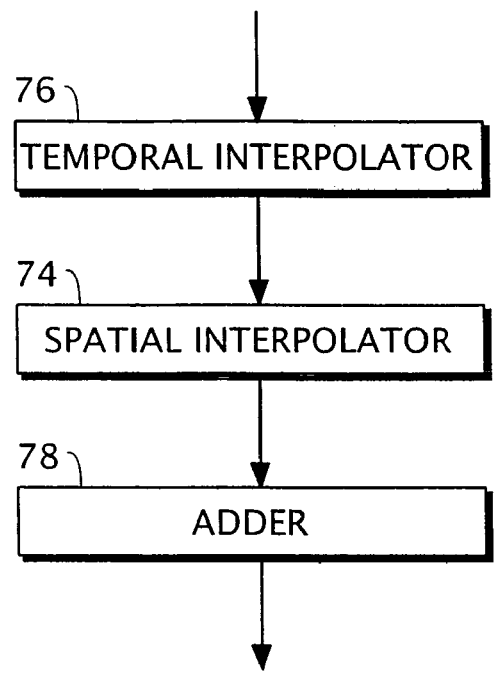
FIG. 5 is a block diagram similar to FIG. 4, showing an alternative configuration of the fine beamformer of FIG. 3.

The image space 42 is divided into a high-resolution grid of voxels. The voxels are spaced more finely than the coarse beams $46_{a1}$, $46_{a2}$, ... $46_{ai}$, $46_{b1}$, $46_{b2}$, ... $46_{bj}$, ... $46_{n1}$, $46_{n2}$, ... $46_{nk}$, nominally at the achievable resolution in cross-range from the synthesized apertures. In FIG. 2B two beam boresights (range lines) $46_{a1}$, $46_{a2}$ and $46_{b1}$, $46_{b2}$ from each of two subapertures $44_a$ and $44_b$, along with four grid points $72_a$, $72_b$, $72_c$, $72_d$, are shown. The intensity at each image point (voxel) $72_a$, $72_b$, $72_c$, $72_d$ is the coherent sum of signals received from the various nearby subaperture-beam shots. The sum is from subapertures across the array, thereby synthesizing a larger aperture. From a given subaperture, each voxel's sum preferably includes the two nearest beams that straddle the given voxel $72_a$, $72_b$, $72_c$, or $72_d$. For example, for voxel $72_d$ and subaperture $44_a$, the two beams $46_{a1}$, and $46_{a2}$ are used. More particularly, signal sample points 73 and 73' are used. The spatial interpolation weight for each of the two beams is such that the pattern of the interpolated beam reaches a maximum (peaks) at the voxel. For image points between the beams, this not only helps the signal-to-noise ratio, but it also reduces the sidelobe pattern of the interpolated beam. Time-interpolation of the signal sample from each shot is also preferably included in the summation at each voxel, as illustrated in FIG. 2B. Various methods for spatial and temporal interpolation known to those skilled in the art all fall within the scope of the fine beamforming method, as does using a different number of beams or time samples for interpolation. FIGS. 4 and 5 illustrate possible modular combinations of a spatial interpolator 74, a temporal interpolator 76, and an adder 78. The result of applying the aforementioned fine beamforming algorithm is that the signal samples from a scatterer at the voxel all peak and add up in phase when summed. The range delay (which determines the phase) for a given voxel's signal sample is equal to the range delay between the subaperture phase center and the voxel. Line 68 (FIG. 2B) represents points with approximately the same range delay to voxel $72_d$ from subaperture $44_a$ and line 70 represents points with approximately the same range delay to voxel $72_d$ from subaperture $44_b$.

As we describe below, our shot machine implementation of the interpolation operations is novel and not obvious, involves precomputations, and is amenable to real-time software implementations.

Figure 6:
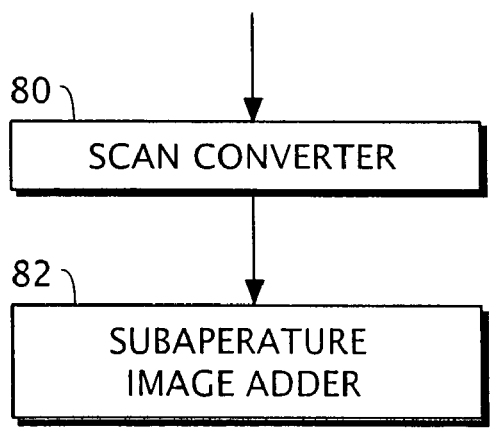
FIG. 6 is a block diagram similar to FIGS. 4 and 5, showing another alternative configuration of the fine beamformer of FIG. 3.

Another preferred embodiment of the fine beamforming algorithm is depicted schematically in FIG. 6. The coarse-resolution range lines from each subaperture $44_a$, $44_b$, ... $44_n$ are scan-converted by a module 80 (using conventional scan conversion algorithms known to those skilled in the art) to the high-resolution Cartesian grid of voxels to form a low-resolution subaperture image. In this operation, the complex nature of the signal (amplitude and phase) is retained. The subaperture images are added together by a module 82 to synthesize a larger aperture, and result in the final, high-resolution image. This addition operation can be with unity weights, or alternatively, non-unity weights to effect a taper. One advantage of this embodiment is that low-resolution images can be created quickly at a high frame rate. Higher and higher-resolution images can be obtained by using more and more subapertures and combining their respective low-resolution images. With the shot machine approach, this allows an image to be built up (from lower-res to higher-res) in time within the total frame time. Successive subaperture images are lower resolution (compared to the final image resolution) and hence highly correlated. As a result, data compression with inherently much higher compression factors should be achievable. This would be extremely useful for telemedicine applications (e.g. mission to Mars) where image data is transmitted remotely, and only low data rate communication is available.

The high-resolution image, once formed using CAC-BF as described above, can be further processed and/or transformed using image processing methods known to those skilled in the art. The image can be rectified (i.e. converted to an amplitude or power) or its real and/or imaginary parts can be processed.

A key advantage of using a CAC-BF approach is that high-resolution beams are obtained in less time for given number of (element) channels. This advantage is demonstrated in the discussion that follows and in greater detail in U.S. patent application Ser. No. 10/353,152 (U.S. patent Publication No. 20030163046).

The volume is covered by the 'product' of subapertures $44_a$, $44_b$, ... $44_n$ and beams $46_{a1}$, $46_{a2}$, ... $46_{ai}$, $46_{b1}$, $46_{b2}$, ... $46_{bj}$, ... $46_{n1}$, $46_{n2}$, ... $46_{nk}$. This can be accomplished with many subapertures, and few beams per subaperture (coarse beams, few elements per beam), or with just a few subapertures, with many beams per subaperture (finer beams, many elements per beam). The product of the two (the total number of beams) is, to first order, independent of subaperture size. Thus with the present method, a certain number of beams $46_{a1}$, $46_{a2}$, ... $46_{ai}$, $46_{b1}$, $46_{b2}$, ... $46_{bj}$, ... $46_{n1}$, $46_{n2}$, ... $46_{nk}$ are required to cover a given volume at a given resolution, and coverage time is proportional to volume/resolution. Once the beams $46_{a1}$, $46_{a2}$, ... $46_{ai}$, $46_{b1}$, $46_{b2}$, ... $46_{bj}$, ... $46_{n1}$, $46_{n2}$, ... $46_{nk}$ are low enough resolution (i.e. they have a small enough number of elements), they only need one shot. Thus one of the key advantages of the method: when down to 1 shot for each beam, we have minimized coverage time. The aforementioned volume can now be imaged in under 0.7 seconds for F/8 in elevation.

One advantage of the present methodology is that the aperture size can be tailored to every grid point $72_a$, $72_b$, $72_c$, $72_d$ (FIG. 2B). The preferred algorithm (using all available intersecting beams) naturally uses more apertures (on both transmit and receive) for grid points at greater ranges. With this embodiment, azimuth resolution (in mm) is constant with range. In a conventional ultrasound, the number of elements making up the aperture is not allowed to grow beyond the number of available channels. In the case of the present invention, the effective aperture can grow to the full size of the physical aperture, exceeding the number of available channels, to the extent limited by the element directivity and desired grating lobe performance.

Another advantage of the CAC-BF beamforming algorithm is that it can be combined with other conventional scanning approaches so that certain parts of a volume to be imaged use CAC-BF beamforming while other parts use conventional beamforming. For example, CAC-BF beamforming could be applied only at further ranges where resolution degrades and conventional beamforming used elsewhere.

We can use conventional shots to fill in the triangular "holes" or blind zones in CAC-BF coverage. These are regions between the subapertures, but outside of their respective scanning extents. The conventional shots use subapertures located between the CAC-BF ones. There is thus the need to transmit a few extra shots, and additional flexibility is needed in the multiplexer and shot selection designs.

Another advantage of the methodology described herein is that better depth of field is obtained with lower resolution beams. This means that an equivalent 3D volume can be covered with fewer shots, or a greater volume can be covered with the same number of shots.

Yet another advantage of the methodology described herein is that better resolution is achieved with the same size aperture (because of the lack of cross-terms). Resolution is two times better than that of a receive-only aperture (i.e. a system that uses a significantly lower resolution transmit aperture), and 1.4 times better than that of a conventional beam using full apertures on transmit and receive. It is to be noted that the full aperture is not normally used on transmit because of the limited depth of field, thus CAC-BF gets almost twice the resolution of conventional systems using the same sized physical aperture. Analyses and experimental measurements show that CAC-BF with 50% overlap performs equivalently to a conventional synthetic aperture of twice its size.

Other variations to the CAC-BF method are described to illustrate the scope of the CAC-BF method in accordance with the present invention.

CAC-BF can be performed with an arbitrary amount of subaperture overlap, recognizing that the resulting image (beam) response characteristics (e.g. the sidelobe behavior including the presence of grating lobes) at an image point will be affected accordingly.

It is to be noted that CAC-BF can be done in two dimensions, or, alternatively, CAC-BF can be performed in one dimension and conventional scanning in the other. CAC-BF can also be used with one-dimensional (1.5D, 1.75D etc.) probes to increase the frame rate for a given number of channels. The frame rate is further improved by the fact that the depth of focus is greater, reducing the number of transmit focii needed. Alternatively, larger effective apertures (better resolution) can be realized without reducing the frame rate. CAC-BF can also be used and tailored to work with systems having virtually any number of receive signal channels. This re-configurability makes CAC-BF well suited as the basis for a an ultrasound system architecture suitable for a whole family of machines.

It is to be noted also that the fine grid within the image space need not be Cartesian and that the coarse beams need not be spaced equally in angle. For example, the beams could be spaced equally in sine-space, or spaced equally in the Cartesian grid. When CAC-BF is applied in both dimensions, the coarse beams could be placed on a grid that is not the product of an azimuth and an elevation grid (e.g. hexagonal or cylindrical scanning).

It is possible to include subaperture cross-terms, in order to improve sidelobes. Moreover, it is possible to transmit from one subaperture only, and receive from the rest of the subapertures. This has the disadvantage of only getting half the resolution per length of aperture, but gets equivalent resolution to CAC-BF per pulse, because aperture overlap is not needed. A potential advantage is a reduction in hardware complexity (may not need transmit multiplexer, or it will be simpler). The reciprocal arrangement (transmit from all subapertures, only receive from middle one) may also be attractive.

Interpolation between beams helps reduce the sidelobes at grid points where the beams from different subapertures don't line up, effectively smoothing the addition of the subapertures at these points. The interpolation can be of any desired amount, using any algorithm known to those skilled in the art. It is possible not to use any interpolation but performance will be affected accordingly.

Shading (windowing) may be done in the summation across the aperture (to reduce sidelobes with narrow-band systems). For similar reasons, or alternatively, the subapertures themselves could be shaded or windowed. Subaperture windowing (weighting applied during the complex summation across subapertures) is an important requirement for achieving low sidelobes with CAC-BF and narrow-band waveforms. Subaperture windowing also helps to reduce the beam response (i.e. gain) in the sidelobe regions when using wideband waveforms.

Windowing in general is state-of-the-art (see Harris, "On the use of windows for harmonic analysis with the discrete Fourier transform", Proc. IEEE, 66, 1, 1978, pp. 51-84). Our innovation is to modify it for CAC image formation. The details below are novel.

Three windowing algorithms are disclosed below in accordance with the present invention. They trade off simplicity with performance. The better, more complex algorithm(s) account for the aperture actually summed at each voxel. With the teaching of these three algorithms, other algorithms will become apparent to those skilled in the art which fall within the spirit of the algorithms described below.

The first simple algorithm windows shots according to their subaperture (independent of beam angle). Thus the outer subapertures have lower weights. This algorithm performs well for voxels far enough away that all subapertures contribute to their signals; it does not control sidelobes for close voxels.

The second simple algorithm windows shots according to their beam angle (independent of subaperture). Thus outer beams have lower weights. This algorithm performs well for voxels close enough that all beam angles contribute to their signals; it does not control sidelobes for far voxels.

More involved algorithms window data according to aperture used (integrated) at each image point. The algorithm accounts for which subapertures contribute to the voxel, and only those. The window weight for a given subaperture is based on its position relative to the total aperture spanned by the contributing subapertures at the voxel. Close ranges only see a subset of the total aperture (but all beam angles); here the algorithm behaves like the beam window. Far ranges only see a subset of the beam angles (but the whole aperture); here the algorithm behaves like the aperture window. Mid ranges and azimuth edges see fractions of either the aperture or the beam angles (or both); the more complicated algorithm ensures low sidelobes at these image points.

If the system hardware response between different shots is unequal, then windowing by itself is not effective. To get low sidelobes with real hardware, we need to account for gain and phase variations across the subapertures and beams. Real systems thus need calibration and equalization. We measure and then invert the hardware's response imperfections (off-line), multiplying shots by stored complex numbers that equalize their responses (on-line).

As we describe below, our shot machine implementation of the windowing and equalization operations, with precomputations, is amenable to real-time software implementations, and allows for a unique weight for each shot's contribution to each voxel.

If shots are simply ordered by aperture or by beam angle, then some regions of the image wait a long time between the shots used in their specific CAC summation. We have a method for ordering the shots used by the CAC algorithm that minimizes the latency at a given range.

The objective is to have any given region be illuminated by shots close together in time, so that the coherent integration is not as affected by motion. Ordering with aperture as outer loop (and beam as inner loop) is optimal for close ranges (i.e. close image regions are illuminated by all their shots nearly consecutively), but the worst case for far ranges. Having beam as outer loop is optimal for far ranges and the worst for close ones.

We have the novel concept of choosing an ordering to be optimal for a particular range or image region. If an intermediate range is chosen, then the worst-case latency (either at short or long ranges) is also reduced. The algorithm simply orders the shots from left to right (or the reverse) as they intersect a given line (e.g. an equi-range line) that crosses the image.

We also have the novel concept of transmitting certain shots more than once, with each one being used in different image regions (where it is closer in time to other shots used in the CAC-BF integration). This makes the frame time longer, but improves image quality. One such method of shot selection divides the image into rectangular strips small in cross-range that extend across all ranges. All shots required to image a given strip are transmitted consecutively. We then move on to another strip (not necessarily adjacent) and image it, completing the frame when all strips have been imaged. Repetition of shots occurs across different strips. Within each strip, shots can be ordered to minimize latency at a particular range as described above.

Each subaperture need not use the same set of scan lines. For example, the subapertures on the edges of the total aperture need not scan outside of the desired image limits. In this way, we further reduce frame time.

The acquired image field of view can be greater than that able to be seen by all subapertures, i.e. we can acquire a larger image, made up of regions contributed to by different fractions of the total aperture. This approach is flexible. We can emulate sector image formats and linear scan formats just by a change in parameters. Our shot machine, software approach to the implementation is highly amenable to this sort of non-uniformity to the processing associated with each subaperture (and image region).

Higher resolution coarse beams (requiring multiple shots) could be utilized, trading off coverage time versus sidelobes. Dynamic focussing may be unnecessary if beams are of low enough resolution (i.e. very small subapetures), and this may reduce complexity.

The 'product' of beams and subapertures need not have each of the nominally 50% overlapping subapertures transmitting all of the coarse beam angles. The product could be formed with a greater number of highly-overlapped subapertures, each transmitting a smaller number (e.g. one) of the beam angles. This has the advantage of having smaller blind zones at the close ranges between the subaperture centers, where no beams are transmitted.

Non-linear or adaptive, high-resolution beamforming techniques are computationally expensive, but may be worthwhile in some applications to combine the multiple subapertures used in the fine beamforming algorithm. The structure of the CAC-BF method is appropriate as there is typically a small number of subapertures. This is not burdensome if it takes a few seconds or minutes to compute; a physician could look at a linearly beamformed image, and suggest an area he would like to see better resolved; then the high-resolution algorithm could be applied.

Coherent Aperture Combining

Programmable, Reconfigurable Shot Machine Approach

The basic algorithm is a shot machine:
1. complex image initialized to zeros (start of frame)
2. loop on shots
3. range filter shot
4. add contribution from given shot to voxels it influences
5. take magnitude of image and display (end of frame)

With the shot machine approach, each shot makes an immediate contribution to the image so that latencies are minimized.

For each shot, we can first do range filtering as a digital convolution of a complex kernel with the received real range line vector. The kernel is the impulse response of the (typically band-pass) range filter. This preserves (and enhances) the amplitude and phase information of the received signal. It is also computationally efficient. The digital convolution can use a two-transform approach, or any other approach that is efficient with the available computing hardware.

The shot machine approach means that each shot's samples can be weighted and added to the various voxels immediately. The addresses of the samples and the voxels are known a-priori, as are the multiplying weights. These weights and addresses (which are the same for every frame) can be pre-computed and stored (for every shot) when initializing for a given image configuration. The weights can include window, interpolation and equalization factors; thus each shot's influence on the image can be computed with a minimum number of multiplies, adds and memory accesses. Thus we can get real time when imaging without needing expensive computing hardware.

Our approach also features easy user-selectable on-the-fly configuration changes to CAC-BF imaging parameters. The turn the knob concept of trading off image resolution, image size, frame rate, and image quality (i.e. vary the number of subapertures, scan limits, and spacing between beams) is a novel feature of our invention. CAC-BF is amenable to a software, programmable, low-cost implementation (already proven) that can allow, for example, large field-of-view imaging followed by zooms at higher resolution, all at the control of the operator.

Thus we can trade off quality (resolution and/or sidelobes) with acquisition time. We can key on certain regions of the image to minimize acquisition time. We can use different subaperture sizes and spacings (in 1 or 2D) optimized for differing image configurations as well as different beams too.

Coherent Aperture Combining Beamforming

2D Scanning

With 2D electronic scanning, the designer has a number of choices for which methods to use in each dimension. The choices include element size (n*lambda, where n can be between 0.5 and 4), what type of scanning (phased, sequenced, CAC-BF), the number of elements in the aperture, and with CAC-BF, the subaperture sizes and overlap. As element size goes up, the cost to achieve a certain level of resolution goes down, but sidelobe performance degrades. Each element size has a maximum achievable resolution, and larger elements have poorer performance. For example, 4-lambda elements cannot do better than about 0.35 mm azimuth resolution, whereas lambda elements can achieve about 0.2 mm azimuth resolution at 7.5 MHz. Systems using CAC-BF in 2D with lambda or 2-lambda elements in both dimensions are viable compromises. With CAC-BF, the larger the subapertures, the costlier (i.e. more channels are needed), but sidelobe performance is better. Once the 1D performance of each alternative is established by testing, then 2D cost/performance/acquisition-time trade-offs can begin. A key feature of the CAC-BF algorithm is that it naturally provides the designer with this cost/performance/acquisition time trade-off.

With 2D CAC-BF, in order to deal with motion within the imaged volume, one can transmit the beams ordered within the volume, i.e. all the beams in top left corner first, then each row left to right, rows ordered top to bottom. In this way, each grid point is illuminated over a short period of time. This is exactly true only in focal plane, grid points at longer or shorter ranges taking somewhat longer to illuminate. The alternative of ordering by subaperture means that every grid point requires the whole sequence of pulses to be imaged. The shot ordering algorithms described above (pick a range with minimum latency, transmit extra shots) are extendable to, and become more important for 2D CAC-BF. Latency is more of a problem because the various image regions must wait for shots to complete the aperture in two dimensions. It is impossible to design a two-dimensional ordering that achieves latencies as small as 1D CAC-BF everywhere. A proposed approach is to select column-shaped image regions, small in azimuth and elevation, but extending across all ranges. All shots required to image a given column are transmitted consecutively. We then move on to another column (not necessarily adjacent) and image it, completing the volume (frame) when all columns have been imaged. Repetition of shots occurs across different columns. Within each column, shots can be ordered to minimize latency at a certain range. In U.S. patent application Ser. No. 10/353,152 (U.S. patent Publication No. 20030163046) (U.S. patent Publication No. 20030163046), we suggest using CAC-BF in one dimension, and conventional scanning in the other (but with larger elements). Doing one CAC-BF slice at a time is better for reduced latency in the coherent image integration. With such a system, the shot ordering would consist of CAC-BF subframes, within which the conventional beam direction (or position) is held constant.

The shot machine approach, windowing, calibration, and interpolation algorithms, programmability, shot selection algorithms, CAC-BF features and advantages that we describe above, all extend fairly obviously to 2D CAC-BF.

The CAC-BF method has been simulated extensively and its performance as described herein validated by these simulations. In addition, experimental results have been obtained by applying CAC-BF in the azimuth dimension as described herein using a 64-channel ultrasound system and a 192-element off-the-shelf probe, suitably programmed to implement the CAC-BF method. The improved resolution, the high-quality imagery, and the reduction in acquisition time compared to conventional beamforming have all been confirmed.

3D Ultrasound Imaging Systems

An ultrasound imaging system in accordance with the present invention provides a novel solution for 3D ultrasound imaging that is affordable, and yet high-performing. Unlike other designs which degrade state-of-the-art imaging performance in order to reduce cost, the present solution maintains or exceeds state-of-the-art imaging performance, while keeping the 3D ultrasound system cost comparable to that of 2D ultrasound systems.

State-of-the-art azimuth imaging performance requires an F number of 2; i.e. an F/2. The F number is the ratio of the focal range divided by the imaging aperture dimension. For example, an F/2 at 5 cm depth requires an instantaneous receive aperture of size 2.5 cm. The present probe is designed to provide an F/2, and an enhanced resolution of F/1 (i.e. twice as good as state-of-the-art).

State-of-the-art elevation imaging performance requires an F/8. The present probe provides a standard elevation resolution of about F/8 and is capable of providing an enhanced elevation resolution of F/4 (twice as good as state-of-the-art) or better.

For state-of-the-art resolutions in both azimuth and elevation, the 2D probe of the present invention (for 3D imaging) is able to acquire a 25 mm×25 mm×70 mm volume electronically in under 1 second. Also, these acquisition times are achievable when just 128 receive channels are available, keeping the number of channels (and hence cost) comparable to state-of-the-art ultrasound imaging systems (for 2D imaging).

This win-win (performance-cost) 3D imaging technology is made possible from the use of the beamforming techniques of the present invention that reduce acquisition time (i.e. the number of shots needed) when the number of received channels available is less than the number of elements in the imaging aperture. The beamforming techniques are referred to as coherent aperture combining beamforming (CAC-BF) as discussed earlier.

In order to reduce the element count and simplify the transducer design, the 2D probe pursuant to the present invention is able to exploit 1.75D elemental technology, with $\lambda$ spacing in azimuth, and $4\lambda$ spacing in elevation in one preferred embodiment.

The 2D probe can be used with conventional beamforming algorithms, as well as with CAC-BF, making it very versatile, saving on the number of probes otherwise required by an ultrasound system. For example, it can operate as a conventional 1D array, employing conventional scanning techniques such as sequential or phased-array scanning in azimuth (or elevation) only.

With CAC-BF, the beamforming can be configured in a number of ways (as described earlier) to reduce the volume acquisition times required, compared to when only conventional beamforming algorithms are used. CAC-BF is performed in azimuth while sequential beamforming is performed in elevation.

The 3D applications were the driving force behind the development of CAC-BF. It is the only way known to the inventors where a significant 3D volume can be imaged with both high resolution and usably short frame times while using currently affordable hardware.

Although the invention has been described in terms of particular embodiments and applications, one of ordinary skill in the art, in light of this teaching, can generate additional embodiments and modifications without departing from the spirit of or exceeding the scope of the claimed invention. While the preferred embodiment described herein represents the form of the invention currently being developed for its carotid artery application, the scope of this invention goes far beyond the form of this preferred embodiment. For example, the CAC-BF solution can be used in the elevation dimension, instead of azimuth, or it could be used in both dimensions, and still be within the scope of the invention. Alternatively, the number and size of elements in each dimension of the transducer could be different, and still fall within the scope of the invention. In the limiting case, the 2D transducer array could collapse to be a 1D array (i.e. designed to scan in only one dimension), and if CAC-BF is used in that single dimension, this configuration is still within the scope of the invention. Accordingly, it is to be understood that the drawings and descriptions herein are proffered by way of example to facilitate comprehension of the invention and should not be construed to limit the scope thereof.

Finally, it is worth re-emphasizing the wide range of applications and systems that can utilize CAC-BF. CAC-BF is well suited for exploitation in low-end, medium-end and premium systems for both 2D and 3D imaging.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for generating image data in an ultrasound scanning process using a coherent-aperture-combining beam-forming or CAC-BF technique, comprising:
   transmitting a set of shots associated with a set of subarrays or subapertures of an available transducer array or aperture in a predetermined sequence;
   receiving echoes of the respective shots;
   coarse beamforming the received echoes to generate a plurality of range lines; and
   fine beamforming the range lines to produce coherent image data,
   the fine beamforming including weighting the range lines.

2. The method defined in claim 1 wherein the fine beamforming further includes range-filtering the range lines prior to the weighting and adding.

3. The method defined in claim 2 wherein the range-filtering includes using a digital range filter with a complex convolution kernel.

4. The method defined in claim 1 wherein the weighting of each range line is carried out immediately upon generation of such range line, the fine beamforming further including adding each weighted range line immediately to a complex coherent image, the weighting of the range lines and the adding of the weighted range lines incrementally to the complex coherent image constituting a shot machine approach continuing until a selected set of shots for a selected set of subarrays or subapertures has been transmitted and the respective resultant range lines weighted and added to the complex coherent image.

5. The method defined in claim 1 wherein the weighting of the range lines includes computing weights and the coherent image addresses for the addition of all shots and storing the computed weights and addresses during an initializing stage prior to real-time imaging.

6. The method defined in claim 1 wherein the transmitting of the shots includes transmitting groups of identical shots in sequence.

7. The method defined in claim 6 wherein respective echoes from each shot in each group of identical shots are coherently processed in a Doppler mode prior to subjecting resultant range line signals to fine beamforming.

8. The method defined in claim 1 wherein the transmitting of the shots includes using a first frequency and the receiving of the echoes includes using a second frequency.

9. The method defined in claim 8 wherein the second frequency is a harmonic of the first frequency to effect a harmonic imaging mode.

10. The method defined in claim 1 wherein the weighting of the range lines includes selecting weights to accomplish spatial interpolating between adjacent beams associated with the same subarray or subaperture.

11. The method defined in claim 1 wherein the weighting of the range lines includes selecting weights to accomplish temporal interpolating between samples.

12. The method defined in claim 1 wherein the weighting of the range lines includes selecting weights to accomplish aperture windowing.

13. The method defined in claim 1 wherein the weighting of the range lines includes selecting weights to accomplish calibrated shot-to-shot equalization.

14. The method defined in claim 1 wherein the weighting of the range lines includes selecting weighting factors associated with spatial and temporal interpolation, aperture windowing, and equalization and combining these factors to minimize floating point operations.

15. The method defined in claim 1, further comprising selecting subapertures, shots and weights in accordance with imaging mode and CAC-BF configuration.

16. The method defined in claim 1, further comprising selecting shots and weights to optimize tradeoffs of measures of imaging performance taken from the group consisting of image size, frame rate, resolution and sidelobes.

17. The method defined in claim 1 wherein weights used in the weighting of the range lines are unit-amplitude.

18. The method defined in claim 1 wherein the weighting of the range lines includes selecting weights to accomplish aperture windowing and further includes selecting a distinct weight for each subaperture at each image voxel that accounts for all subapertures that contribute to the voxel.

19. The method defined in claim 1 wherein the transmitting of the shots includes ordering or sequencing the transmitted shots to minimize latency in coherent image data formation at a given range.

20. The method defined in claim 1 wherein the transmitting of the shots includes re-transmitting certain shots in order to reduce latency in coherent image data formation at certain image regions.

21. The method defined in claim 1 wherein the transmitting of the shots includes sequencing the shots so that a particular planar region is filled with consecutive shots, thereby reducing latency with 1D CAC-BF for that region.

22. The method defined in claim 1 wherein the transmitting of the shots includes sequencing the shots so that a particular volumetric region is filled with consecutive shots, thereby reducing latency with 2D CAC-BF for that region.

23. The method defined in claim 1 wherein the weighting includes calibrating and equalizing weights that account for gain and phase differences in the received echoes due to hardware imperfections associated with the transmission of shots or the reception of the received echoes.

24. The method defined in claim 1 wherein the transmitting of the shots includes transmitting extra shots to cover the short-range blind zones in CAC-BF coverage.

25. The method defined in claim 1 wherein the transmitting of the shots includes omitting shots directed outside of a preselected image region.

26. A system for gathering ultrasound image data in a scanning process, comprising:
   a probe having an array of transducer elements;
   switching electronics operatively connected to the probe for selectively energizing the transducer elements and selectively polling the transducer elements to effectively divide the array into a plurality of subapertures each transmitting shots and receiving respective echoes; and a signal processor operatively connected to the transducer elements (a) to process the echoes to form a plurality of respective low-resolution ultrasound beam signals that span a volume to be imaged, (b) to weight the beam signals to improve resulting image data quality, and (c) to combine the weighted beam signals in a fine beamforming process to generate coherent image data with a synthesized aperture larger than any one of the subapertures and focused at each data point of the volume.

27. The system defined in claim 26 wherein the signal processor carries out a coherent-aperture-combining beamforming or CAC-BF method, the subapertures and shots being programmable for different modes and CAC-BF configurations.

28. The system defined in claim 26 wherein the signal processor carries out a coherent-aperture-combining beamforming or CAC-BF method, the different modes and CAC-BF configurations being operator-selectable.

29. The system defined in claim 26 where the signal processor is programmable.

* * * * *